United States Patent
Avny et al.

[19]

[11] Patent Number: 5,819,736
[45] Date of Patent: Oct. 13, 1998

[54] VIEWING METHOD AND APPARATUS PARTICULARLY USEFUL FOR VIEWING THE INTERIOR OF THE LARGE INTESTINE

[75] Inventors: Arie Avny, Rehovot; Avi Raz, Yavne; Giora Bernat, Haifa, all of Israel

[73] Assignee: Sightline Technologies Ltd., Haifa, Israel

[21] Appl. No.: 408,077

[22] Filed: Mar. 22, 1995

[30]     Foreign Application Priority Data

Mar. 24, 1994 [IL] Israel ......................................... 109121
Dec. 30, 1994 [IL] Israel ......................................... 112209

[51] Int. Cl.⁶ ...................................................... A61B 5/05
[52] U.S. Cl. ......................................... 128/653.1; 128/665
[58] Field of Search ................................. 128/653.1, 664, 128/665; 356/426–428, 241; 600/114–116

[56]              References Cited

U.S. PATENT DOCUMENTS

| | | | |
|---|---|---|---|
| 4,561,427 | 12/1985 | Takada ..................................... | 600/114 |
| 4,967,092 | 10/1990 | Fraignier et al. ........................ | 356/241 |
| 5,090,259 | 2/1992 | Shishido et al. ......................... | 356/241 |
| 5,188,111 | 2/1993 | Yates et al. .............................. | 128/657 |
| 5,365,331 | 11/1994 | Tamburrino et al. .................... | 356/241 |
| 5,398,670 | 3/1995 | Ortiz et al. .............................. | 600/114 |

FOREIGN PATENT DOCUMENTS

| | | |
|---|---|---|
| 80 10672 | 5/1980 | France . |
| 34 40 177 | 5/1986 | Germany . |
| 86/06944 | 12/1986 | WIPO . |
| 94/05200 | 3/1994 | WIPO . |

*Primary Examiner*—Brian L. Casler
*Attorney, Agent, or Firm*—Ladas & Parry

[57]              ABSTRACT

An optical viewing device includes a housing of a size and shape for introduction into the large intestine of a subject and for movement therein in either direction, and an image transducer located within the housing for converting optical images into electrical signals. Various embodiments are described in which the housing is of a size and shape for movement by its own weight in either direction in the intestine, or in which the housing includes an electric motor driving propelling means for propelling the housing through the intestine, or in which the housing is carried at one end of a rod of a length such that a user may grasp the opposite end and manipulate the housing to scan the interior surface of the intestine.

18 Claims, 4 Drawing Sheets

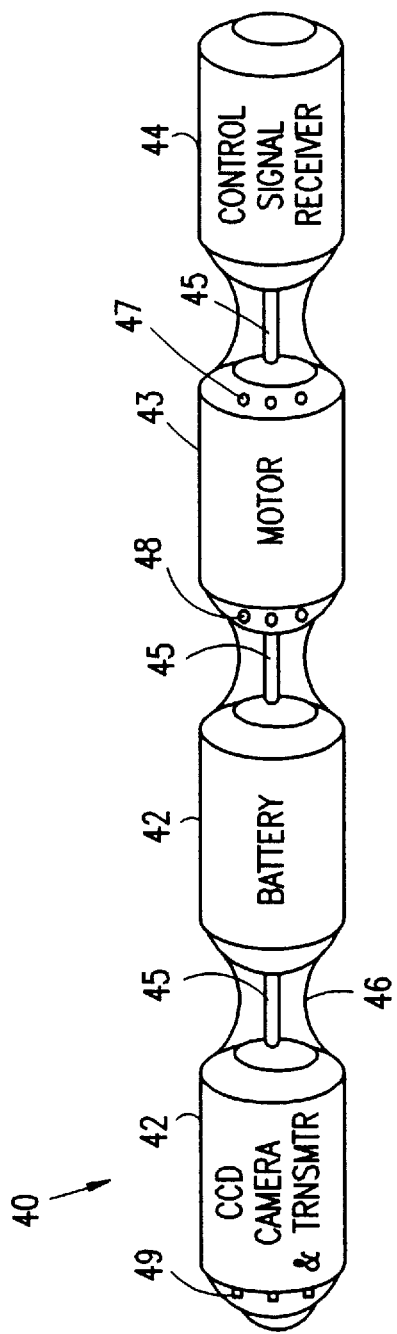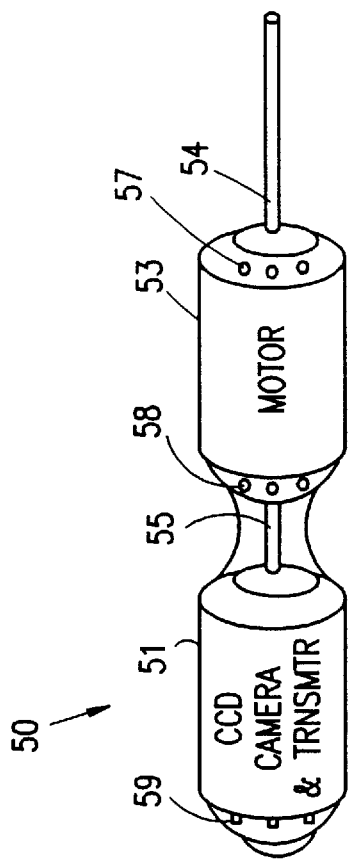

VIEWING METHOD AND APPARATUS PARTICULARLY USEFUL FOR VIEWING THE INTERIOR OF THE LARGE INTESTINE

FIELD AND BACKGROUND OF THE INVENTION

The present invention relates to a method and apparatus for viewing the interior surfaces of a cavity. The invention is particularly useful for viewing the interior surfaces of a subject's intestine, and is therefore described below particularly with respect to this application.

Colonic malignant tumor is the main cancer in the Western countries. Its precursor, the benign polyp, is formed in about 15% of the adult population. Early detection of the polyp is therefore critical for the prevention and treatment of this type of cancer.

A common technique for colonic tumor detection is a barium enema. Barium sulfate is introduced as a contrast material through the anus and fills the entire large bowel. X-rays are used to make pictures of the whole abdominal contents, including the opaqued large bowel. Such a test, however, is unpleasant, inaccurate, causes subject's inactivation, and requires the presence of a physician.

Another technique uses a colonoscope which is inserted via the subject's anus into the colon to allow the physician to view the interior of the colon and rectum. This technique, however, not only must be performed by a physician, but is also time consuming and painful such that it frequently requires administering a pain relieving agent to the patient.

A further technique for inspecting the interior of the colon is by ultrasound, but this method must also be performed by a physician; moreover, in its present pilot study stage, it is less accurate than the other two methods.

OBJECTS AND BRIEF SUMMARY OF THE INVENTION

A broad object of the present invention is to provide a novel method and apparatus for viewing the interior surfaces of a cavity. A more particular object is to provide a novel method and apparatus for visually inspecting the interior of a cavity in the human body, such as the large intestine, to enable early detection of polyps so that they can be removed while still in the benign stage, or as soon as possible after they have become malignant. The method and apparatus may also be used for viewing the interior of other cavities.

According to one aspect of the present invention, there is provided a method of viewing the interior surfaces of a cavity in an object, comprising: introducing into the cavity an optical viewing device including a housing containing an image transducer for converting optical images into electrical signals; manipulating the object to direct the optical viewing device by its own weight to scan the surfaces of the cavity interior to be viewed; and reconverting the electrical signals to optical images.

The invention is particularly applicable for visually inspecting the interior surface of a cavity in the human body, such as the large intestine. When so used, the optical viewing device can be applied as conveniently and relatively painlessly as a suppository inserted into the rectum and can be steered to scan the interior surfaces of the large intestine by appropriately manipulating the table on which the subject is fixed.

According to further features in the preferred embodiment of the invention described below, the optical viewing device further includes a transmitter within its housing for transmitting electrical signals from the image transducer externally of the subject, there being a video receiver in the vicinity of the subject to receive the transmitted electrical signals and to convert them to optical images for viewing in a real time manner by the attendant. It is conceivable, however, that with the rapid development of miniaturized electronic memories, the optical viewing device could also store within it the electrical signals from the image transducer and reproduce the optical images after the device has been expelled from the subject's body.

According to further features in the preferred embodiments of the invention described below, a liquid is introduced into the cavity, e.g., the colon, in order to inflate it before introducing the optical viewing device. This feature better permits the optical viewing device to be steered to scan the internal surfaces of interest by manipulating the table supporting the subject in order to direct the optical viewing device through the cavity by the weight of the optical viewing device.

The foregoing method provides a number of important advantages over the existing methods when used for visually inspecting the internal surface of a subject's intestine. Thus, the method may be done quickly and substantially painlessly and generally would not require the administration of a pain relieving agent. The procedure can also be performed by a nurse and would normally not require the presence of a physician. One nurse can easily administer the test to a number of patients at the same time. In addition, the method permits viewing the interior of the subject's intestine in a real time manner at the time the examination is made. It also permits the results of the examination to be recorded for later viewing, e.g., to enable consultation with others if desired.

According to further features, an inflatable balloon may also be introduced into the cavity in deflated condition and then inflated to retain the liquid within the cavity while the optical device scans the cavity.

According to other aspects, the invention also provides optical viewing devices moved by a motor included within such device, or a rod atached to the device.

BRIEF DESCRIPTION OF THE DRAWINGS

Further features and advantages will be apparent from the description below.

The invention is herein described, by way of example only, with reference to the accompanying drawings, wherein:

FIG. 4 illustrates another form of optical viewing device constructed in accordance with the invention;

FIG. 5 illustrates an alternative construction of such an optical viewing device;

DESCRIPTION OF PREFERRED EMBODIMENTS

Figure 1:
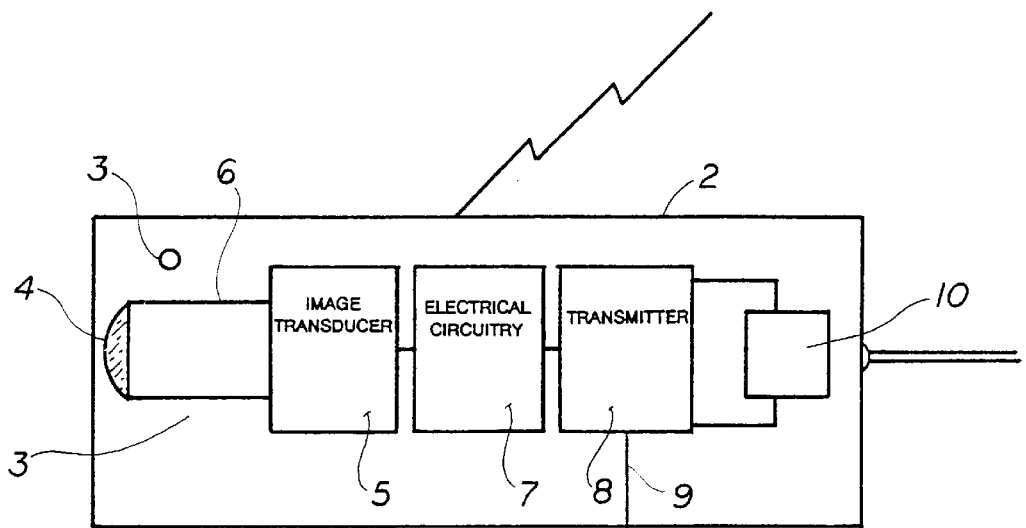
FIG. 1 schematically illustrates one form of optical viewing device constructed in accordance with the present invention.

FIG. 1 schematically illustrates an optical viewing device which includes a housing 2 made of a suitable material which can be inserted into the rectum of a subject in the manner of a suppository. Housing 2 is hydrodynamically shaped with all smooth surfaces so that it can move freely in both directions through the rectum and colon of the subject, as will be described more particularly below.

The front end of the housing carries illuminating means 3, e.g., LEDs (light emitting diodes) which illuminate the tissue to be optically viewed. The front end of housing 2 further includes a lens 4 for receiving the light from the tissue being viewed and for focusing it on an image transducer 5, such as a CCD (charge couple device), commonly used in solid-state television cameras. An opaque shield 6 between focusing lens 4 and the image transducer 5 prevents stray light from being received on the image transducer.

The image transducer 5 converts the images focused on it by focusing lens 4 into electrical signals. These electrical signals are outputted to electrical circuitry, schematically indicated at 7 within the housing 2. Electrical ciruitry 7 would include the conventional circuitry as used in solid-state television cameras to control the scanning, amplifying and modulating of the electrical signals outputted by the image transducer 5. The modulating electrical signal is then fed to a transmitter 8 within housing 2 which transmits the electrical signals externally of the subject via an antenna 9. The illustrated electrical components are powered by a self-chargeable battery 10 located within housing 2.

Figure 2:
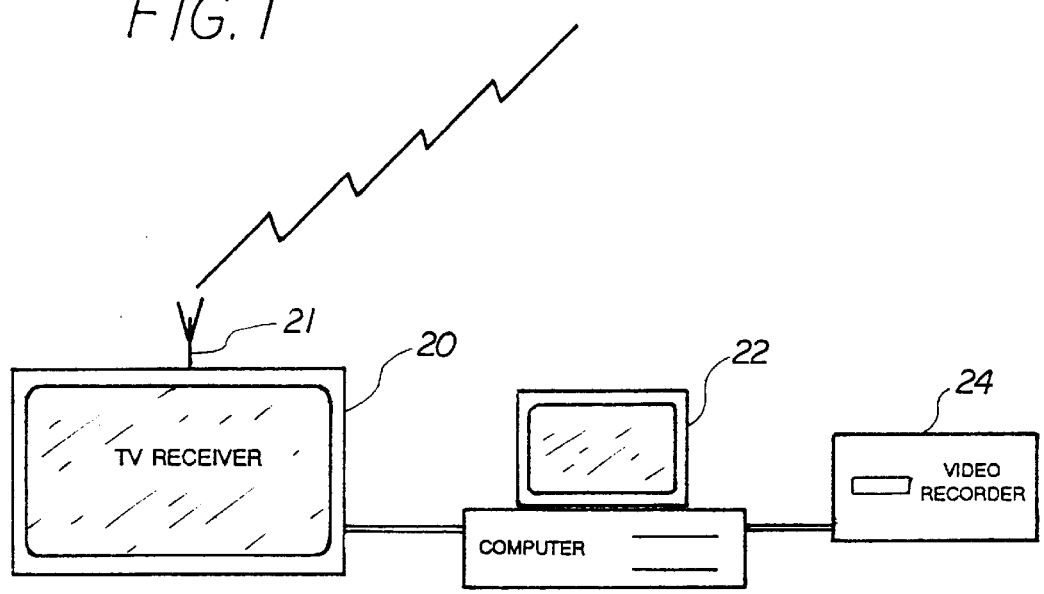
FIG. 2 illustrates the external apparatus that may be used with the optical viewing device of FIG. 1.

FIG. 2 illustrates the equipment for receiving the electrical signals transmitted by the optical viewing device of FIG. 1. This equipment also converts such electrical signals to an optical image for real-time viewing and/or for recording to enable viewing at a later time. The equipment illustrated in FIG. 2 includes a television receiver 20 having an antenna 21 for receiving the electrical signals transmitted by the transmitter 8 of the optical viewing device shown in FIG. 1. Also illustrated in FIG. 2 are a computer 22 connected to the television receiver 20 in order to receive and process the information if necessary, and a video recorder 24 for recording the information if desired for later viewing.

All the components illustrated in FIGS. 1 and 2 are well known components, and therefore their constructions are not set forth in detal.

It will thus be seen that the optical viewing device shown in FIG. 1 may be administered to the subject via the rectum, in the manner of a suppository. In order to direct the optical viewing device to scan the surfaces of the colon and rectum desired to be inspected, the colon of the subject is first filled with a liquid, such as water, to inflate the colon before the device is introduced via the subject's anus.

Figure 3:
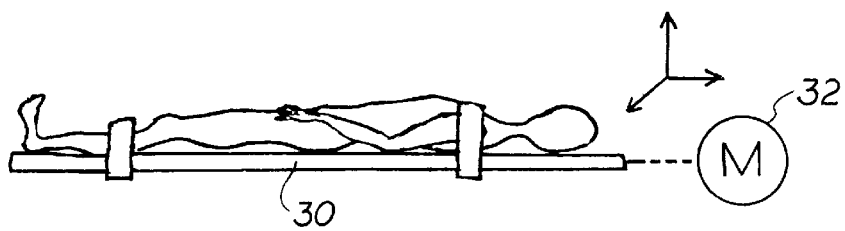
FIG. 3 schematically illustrates the manner of manipulating the supporting table on which the patient is fixed at the time of the test in order to steer the optical viewing device of FIG. 1 by its own weight to scan the surfaces desired to be visually inspected.

The subject is preferably first secured on a table, as shown at 30 in FIG. 3. The table may then be manipulated by a drive, schematically shown at 32, in order to orient the subject to the different positions for directing the optical viewing device by its own weight to scan the surfaces of the colon desired to be viewed.

As the optical viewing device is thus scanning the surfaces, the electrical signals outputted by image transducer 5 are transmitted by transmitter 8 and antenna 9 externally of the subject and are received via antenna 21 of the video receiver 20 for display on the video receiver. The received electrical signals are also fed to computer 22 for processing if desired, and to video recorder 24 for storage to enable later viewing if desired.

After the examination has been completed, the optical viewing device illustrated in FIG. 1 may be expelled in the normal manner from the subject's body.

The optical viewing device illustrated in FIG. 4, and therein designated 40, includes a first section 41 containing an image transducer, e.g., a CCD camera, and a transmitter; a second section 42 containing an internal battery; a third section 43 containing a motor for propelling the optical viewing device 40; and a fourth section 44 containing a control signal receiver for controlling the operation of the motor in section 43. Sections 41–44 are attached to each other by flexible connections 45, and are all enclosed within a flexible cover shown schematically at 46.

The motor in section 43 propels the optical viewing device 40 in the forward direction by reaction jets discharged through openings 47 in the rear end of that section, and in the reverse direction by similar reaction jets discharged via openings 48 in the forward end of that section. Control of the motor is effected by signals received via the control signal receiver section 44 and transmitted from an external location, e.g., via an RF transmitter. The front end of the optical viewing device 40 is provided with a plurality of light sources, e.g., an annular array of LEDs, to illuminate the surfaces scanned by the CCD camera within section 41. This information is transmitted via a transmitter in section 41 to a remote location; alternatively, section 41 may include a high-density semi-conductor storage device for storing this information, enabling the information to be read out after the optical viewing device 40 has been removed from the subject.

It will thus be seen that the motor in section 43 propels the optical viewing device 40 either forwardly or reversely as the CCD camera 41 scans the surfaces to be inspected, e.g., the colon and rectum. The flexible connections 45 between the various sections permits the device as a whole to worm its way through the cavity (e.g., colon) being inspected, while the outer flexible covering 46 protects the device from body fluids as well as from the water used for inflating the body cavity being inspected.

FIG. 5 illustrates an alternative optical viewing device, generally designated 50, which may be used. This device includes a front section 51 containing the CCD camera and transmitter, and a motor section 53 containing the motor for propelling the device through the body cavity. The device illustrated in FIG. 5, however, does not contain a battery section (corresponding to section 42, FIG. 4), or a control signal receiver section (corresponding to section 44, FIG. 4), but rather an electrical conductor 54 which supplies the electrical power and the control signals to the motor section 53 from an external source. Conductor 54 is flexible to permit the optical viewing device to freely travel through the cavity of the subject. It may also serve as a channel for the electrical signals transmitted from the transmitter within section 51 to an external monitoring unit.

In all other respects, the optical viewing device 50 shown in FIG. 5 is constructed as described above with respect to FIG. 4, including a flexible connection 55 between the two sections 51 and 53, jet openings 57 at the rear end of section 53 for propelling the unit forwardly, jet openings 58 at the front end of section 53 for propelling the unit reversely, and an annular array of LEDs 59 at the front of the CCD camera section 51.

Figure 6:
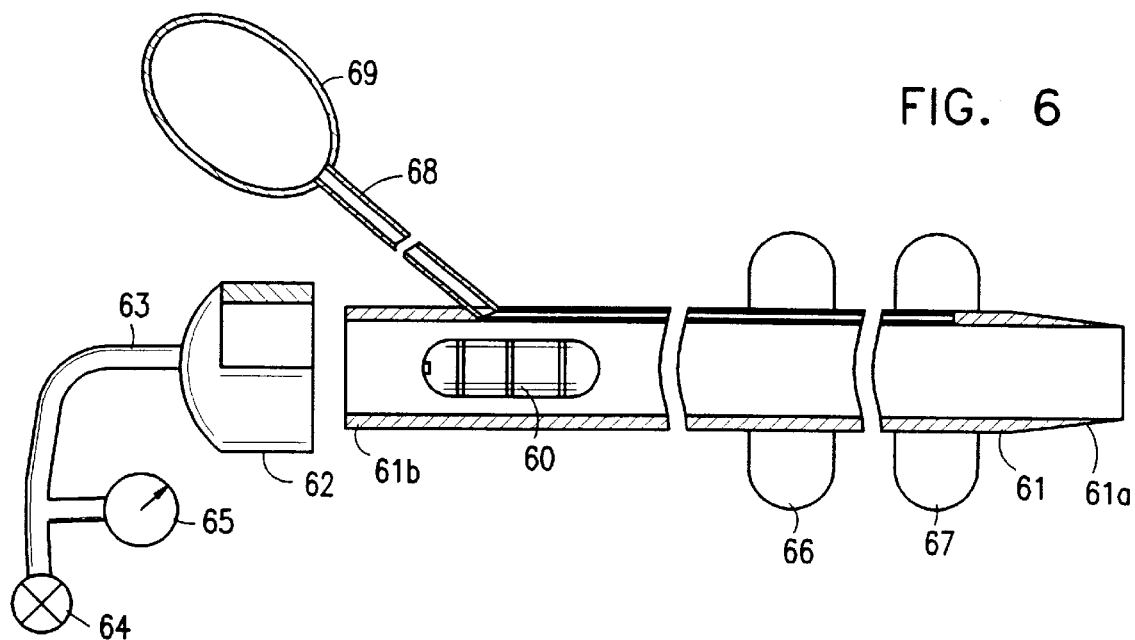
FIG. 6 illustrates another form of apparatus constructed in accordance with the invention.

FIG. 6 illustrates one form of overall apparatus that may be used for introducing the optical viewing device, generally designated 60, into the body cavity, e.g., the large intestine, to be inspected. The apparatus illustrated in FIG. 6 includes a hollow rectal tube 61 having a tapered front end 61a to facilitate its insertion via the subject's anus into the subject's rectum. The opposite end 61b of rectal tube 61 receives a connector 62 connected by a water tube 63 to a source of pressurized water 64, which water is introduced into the rectum and colon as described earlier. A gauge 65 measures the water pressure.

Rectal tube 61 further includes two annular balloons 66, 67 secured to the outer surface of the tube at spaced locations along its length. When rectal tube 61 is inserted, the two balloons are in a deflated condition, but after the tube has been inserted, the two balloons are inflated by another fluid, preferably air, via an air tube 68 connected to a hand pump 69 which is to be located externally of the subject.

After the two annular balloons 66, 67 have thus been inflated, pressurized water may then be introduced via water tube 63 and rectal tube 61 into the subject's rectum and colon to inflate them so that the balloons retain the water within the cavity while the cavity is inspected by the optical viewing device 60. Device 60 may be moved through the rectum and colon by manipulating the subject as described in patent application Ser. No. 109121, or by a propulsion system included with the optical viewing device, as described above with respect to FIGS. 4 and 5.

After the inspection has been completed, the optical viewing device would normally be removable by the natural peristaltic movements of the intestine. Nevertheless, FIGS. 7 and 8 illustrate two possible manners of facilitating the removal of this device, and particularly for assuring that it will be properly oriented at the time of its removal.

Figure 7:
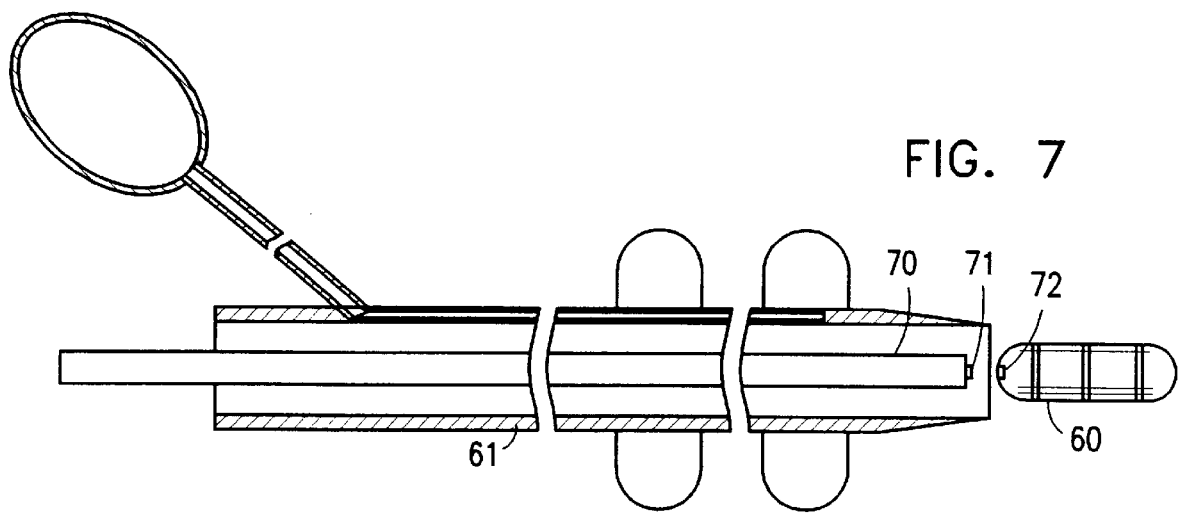
FIGS. 7 and 8 are fragmentary views illustrating variations in the construction of the apparatus of FIG. 6.

FIG. 7 illustrates one manner of aiding the removal of the optical viewing device 60 from the subject. In this case, the optical viewing device is removed from the cavity with the aid of a rod 70 passed through the rectal tube 61 and having a magnet 71 at one end to be magnetically coupled to a magnet 72 carried by the rear end of the optical viewing device 60.

Figure 8:
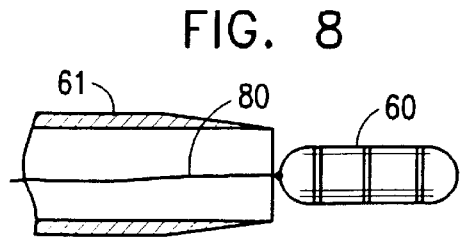

FIG. 8 illustrates a tether arrangement that may be used for removing the optical viewing device 60. The arrangement illustrated in FIG. 5 includes a flexible cord 80 passed through the rectal tube 61 and attached to the optical viewing device 60, so that the device can be extracted by merely pulling the cord via the rectal tube 61.

Figure 9:
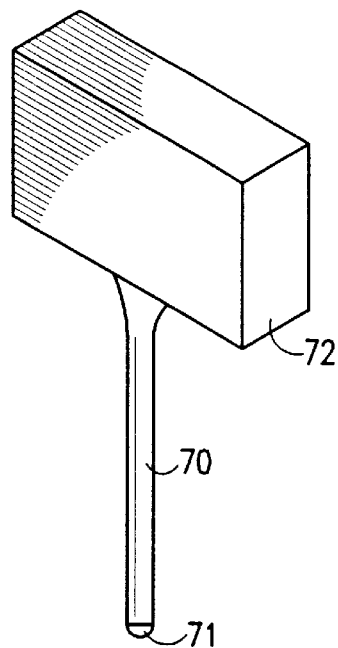
FIGS. 9 and 10 illustrate further optical viewing devices constructed in accordance with the invention.
Figure 10:
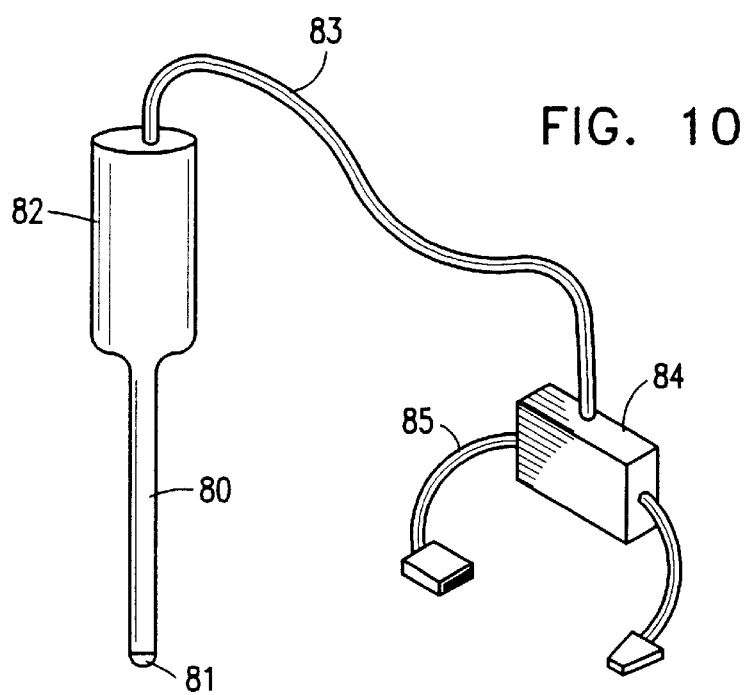

FIGS. 9 and 10 illustrate two further optical viewing devices that may be used for inspecting interior surfaces of body cavities.

The optical viewing device illustrated in FIG. 9 includes a rod 70 having at one end an image transducer 71 for converting light images into electrical signals. Image transducer 71 includes the necessary optical lenses for focussing the image, and also a light source for illuminating the surface to be viewed. Rod 70 is of a length such that a user may grasp the rod, insert the image transducer 71 into the body cavity, and manipulate the image transducer from the opposite end, externally of the body cavity, to scan the interior surface of the cavity to be inspected.

The opposite end of rod 70 to be disposed externally of the body cavity includes a housing 72 which houses the power supply and circitry for converting the electrical signals from the image transducer 71 to video signals. Housing 72 may also include a transmitter for transmitting the video signals to a remotely-located monitor (not shown).

FIG. 10 illustrates a variation, also including a rod 80 carrying an image transducer 81 at one end as in FIG. 9. The opposite end 82 of the rod, to be disposed externally of the body cavity, is connected by electrical wires 83 to a housing 84 carried by a wristband 85 to be worn by the user. Housing 84 on wristband 85 contains the power supply and the electrical circitry for converting the electrical signals from the image transducer 81 to video signals to be reproduced in a monitor (not shown). Housing 84 may also include a transmitter for transmitting the video signals to a remotely-located monitor.

While the invention has been described with respect to one construction and one application, particularly for making colon and rectum examinations, it is to be appreciated that this is merely one example of an application of the invention, and that the invention may be used in other applications. Many other variations and applications of the invention will be apparent.

We claim:

1. A method of viewing the interior surfaces of a cavity in an object comprising: introducing into said cavity an optical viewing device including a housing containing an image transducer for converting optical images into electrical signals; manipulating the object to direct the optical viewing device by its own weight to scan the surfaces of the cavity interior to be viewed; and reconverting said electrical signals to optical images, wherein said cavity is filled with a liquid before introducing said optical viewing device therein.

2. The method according to claim 1, wherein said electrical signals are reconverted to optical images by transmitting the electrical signals from said image transducer externally of the object; receiving said transmitted electrical signals; and converting said electrical signals to optical images.

3. The method according to claim 1, wherein said optical viewing device further includes an artificial light source for illuminating said cavity interior surfaces to be viewed.

4. The method according to claim 1, wherein said cavity is defined by a deformable wall, and said cavity is filled with said liquid to inflate said wall before introducing said optical viewing device therein.

5. The method according to claim 1, wherein the optical viewing device is extracted from the body cavity by means of a rod having a first magnet at one end thereof introduced into the cavity, cooperable with a second magnet carried by the optical viewing device.

6. The method according to claim 1, wherein the optical viewing device is extracted from the cavity by means of a flexible cord attached to the optical viewing device.

7. A method of visually inspecting the interior surface of a body cavity, particularly the large intestine, of a subject comprising: introducing into the subject's large intestine, via the anus, an optical viewing device including a housing containing an artificial light source for illuminating the surface to be inspected, an image transducer for converting optical images into electrical signals, and a focusing lens for focusing the optical images onto the image transducer; moving the optical viewing device to scan the surface to be inspected for obtaining an optical image thereof; converting the optical image into electrical signals; and reconverting said electrical signals of the image transducer to optical images, wherein a liquid is introduced into said large intestine before introducing said optical viewing device.

8. The method according to claim 7, wherein said optical viewing device is moved through the large intestine by manipulating the subject to different orientations to cause the optical viewing device to move by its own weight.

9. The method according to claim 7, wherein said optical viewing device is moved through the large intestine by a motor included in said optical viewing device.

10. The method according to claim 7, wherein an inflatable balloon is also introduced into said body cavity in deflated condition and then inflated to retain said liquid within the body cavity while the optical viewing device scans the body cavity.

11. The method according to claim 10, wherein said inflatable balloon is of annular configuration and is attached to the outer surface of a hollow tube inserted into the body cavity and through which the liquid and the optical viewing device are introduced into the body cavity.

12. The method according to claim 11, wherein the hollow tube is introduced into said body cavity with two of said inflatable balloons attached to its outer surface in spaced relation to each other and said two of said inflatable balloons are inflated subsequent to introduction of said tube into said body cavity.

13. An optical viewing device, comprising:
   a self-propelled housing of a size and shape for introduction into the large intestine of a subject and for movement therein in either direction; an image transducer located within said housing for converting optical images into electrical signals when a liquid is introduced into said large intestine before introducing said optical viewing device.

14. The device according to claim 13, wherein said housing is of a size and shape for movement by its own weight in either direction in said intestine.

15. The device according to claim 13, wherein said housing further includes an electric motor driving propelling means for propelling the housing through said intestine.

16. The device according to claim 13, wherein said housing is carried at one end of a rod, said rod being of a length such that a user may grasp the opposite end, insert the housing into the intestine, and manipulate the housing from said opposite end externally of the body cavity to scan the interior surface of the intestine.

17. The device according to claim 16, wherein said one end of the rod also includes a light source for illuminating the surface to be viewed.

18. The device according to claim 17, wherein said opposite end of the rod includes a housing containing electrical circuitry and a power supply for receiving said electrical signals and for processing them into video signals.

* * * * *